(12) United States Patent
Farnebo et al.

(10) Patent No.: US 7,902,167 B2
(45) Date of Patent: Mar. 8, 2011

(54) COMPOUNDS AND METHODS FOR DOWN-REGULATING WRAP53 PROTEIN BY RNA INTERFERENCE

(75) Inventors: Marianne Farnebo, Stockholm (SE); Salah Mahmoudi, Stockholm (SE); Klas Wiman, Täby (SE)

(73) Assignee: Aprea AB, Stockholm (SE)

( * ) Notice: Subject to any disclaimer, the term of this patent is extended or adjusted under 35 U.S.C. 154(b) by 0 days.

(21) Appl. No.: 12/444,043

(22) PCT Filed: Oct. 1, 2007

(86) PCT No.: PCT/SE2007/050692
§ 371 (c)(1), (2), (4) Date: Apr. 2, 2009

(87) PCT Pub. No.: WO2008/041933
PCT Pub. Date: Apr. 10, 2008

(65) Prior Publication Data
US 2010/0113558 A1    May 6, 2010

Related U.S. Application Data

(60) Provisional application No. 60/848,402, filed on Oct. 2, 2006.

(30) Foreign Application Priority Data

Oct. 2, 2006  (SE) .................................. 0602041

(51) Int. Cl.
  *A61K 31/70*  (2006.01)
  *C07H 21/04*  (2006.01)
(52) U.S. Cl. ......................... 514/44; 536/23.1; 536/24.5
(58) Field of Classification Search .................. None
  See application file for complete search history.

(56) References Cited

U.S. PATENT DOCUMENTS

| 6,943,241 | B2 | 9/2005 | Isogai et al. | |
|---|---|---|---|---|
| 2006/0025361 | A1 | 2/2006 | McSwiggen et al. | |
| 2006/0035815 | A1 | 2/2006 | Chen et al. | |
| 2006/0063174 | A1 | 3/2006 | Turner et al. | |
| 2006/0069056 | A1* | 3/2006 | Feinstein et al. | 514/44 |
| 2007/0104688 | A1* | 5/2007 | Rossi et al. | 424/93.2 |
| 2009/0149377 | A1* | 6/2009 | Takagi et al. | 514/12 |

FOREIGN PATENT DOCUMENTS

| WO | 93/23569 A1 | 11/1993 |
|---|---|---|
| WO | 94/02595 A1 | 2/1994 |
| WO | 99/04819 A1 | 2/1999 |
| WO | 99/05094 A1 | 2/1999 |
| WO | 2004097020 A2 | 11/2004 |

OTHER PUBLICATIONS

Mahmoudi et al. Molecular Cell 2009, vol. 33, pp. 462-471.*
Lockshin and Zakeri, Programmed cell death and apoptosis:origins of the theory, Nat Rev Mol Cell Bio, (2) p. 545-50, 2001.
Velazquez-Fernandez et al., Differential RNA expression profile by cDNA microarray in sporadic primary hyperparathyroidism (pHPT): primary parathyroid hyperplasia versus adenoma, World Journal of Surg, 30 (5):705-712, May 20, 2006; (XP-002489844).
Zhang, GEPIS-quantitative gene expression profiling in normal and cancer tissues, Bioinformatics, (20) p. 2390-8, 2004; (XP-002489845).
Fu, Roles of aurora kinases in mitosis and tumorigenesis, Mol Cancer Res, (5) p. 1-10, 2007.
Zamore et al., RNAi: Double-stranded RNA directs the ATP-dependent cleavage of mRNA at 21 to 23 nucleotide intervals, 2000, Cell, 101, 25-33.
Fire et al., Potent and specific genetic interference by double-stranded RNA in Caenorhabditis elegans, 1998, Nature, 391,806.
Sharp, RNAi and double-strand RNA, 1999, Genes & Dev., 13:139-141 .
Strauss, Molecular biology: Candidate 'gene silencers' found,1999, Science, 286, 886.
A. E. Pasquinelli et al., Conservation of the sequence and temporal expression of let-7 heterochronic regulatory RNA, Nature 408, 86 (2000).
Scaringe et al, Novel RNA synthesis method using 5'-O-Silyl-2'-O-orthoester protecting groups, J. Am. Chem. Soc. 120:11820 (1998).
Song et al., RNA interference targeting FAS protects mice from fulminant hepatitis, Nat. Med, 2003, 9:347-351.
Li et al., Using siRNA in prophylactic and therapeutic regimens against SARS coronavirus in Rhesus macaque, Nat. Med, 2005, 11:944-951.
Quinlan, E. (2005) ARVO Annual Meeting, May 1-5, Ft Lauderdale, FL, USA.
Farnebo, Examensarbete, Internet Article, pp. 1-2 (2007).
Database uniProt, WD repeat-containing protein 79 (2001).

* cited by examiner

*Primary Examiner* — Tracy Vivlemore
(74) *Attorney, Agent, or Firm* — Browdy and Neimark, PLLC (57) ABSTRACT

A small nucleic acid molecule that down-regulates expression of Wrap53 gene via RNA interference (RNAi), wherein at least one strand of said small nucleic acid molecule is about 15 to about 30 nucleotides in length; and wherein at least one strand of said small nucleic acid molecule comprises a nucleotide sequence having sufficient complementarity to an RNA of said Wrap53 gene for the small nucleic acid molecule to direct cleavage of said RNA via RNA interference, for use as a medicament.

20 Claims, 7 Drawing Sheets

Fig. 1.

| siWrap53-E9 target sequence | AATCAGCGCATCTACTTCGAT |
|---|---|
| siWrap53-W2 target sequence | AACGGGAGCCTTTCTGAAGAA |

Fig. 2.

Lane:
1. Untreated U2OS cells
2. Only oligofectamine treatment
3. siControl treatment
4. siWrap53-E9 treatment 140 ng/well (6-well plate)
5. siWrap53-E9 treatment 420 ng/well

Fig. 3.

Lane:
1. siControl treatment 10nM
2. siWrap53-W2 treatment 10nM

Fig. 4.

U2OS cells

Fig. 5

Saos-2 cells

Fig. 6.

Lane:
1. Unsyncronized U2OS cells
2. G1 blocked cells (Aphidocolin)
3. G2/M blocked cells (Nocodazole)

H1299 cells (lung cancer), si*Wrap53* for 72 hours

COMPOUNDS AND METHODS FOR DOWN-REGULATING WRAP53 PROTEIN BY RNA INTERFERENCE

FIELD OF THE INVENTION

The present invention relates to therapeutic treatment of hyperproliferative disorders, including cancer. In particular, the present invention relates to small nucleic acid molecules capable of reducing the expression of a gene termed Wrap53 for the treatment of hyperproliferative disorders.

BACKGROUND OF THE INVENTION

Over the past decades, it has become clear that cells die in an ordered fashion during normal development. This ordered scheme of dying is a very well conserved process termed programmed cell death or apoptosis.

Apoptosis serves as a major mechanism for removal of unwanted and potentially dangerous cells, such as virus-infected cells, self-reacting cells and tumor cells (Lockshin and Zakeri, Nat Rev Mol Cell Bio, (2) p 545-50, 2001). Many hyperproliferative diseases, including cancer, are caused by dysfunction in the apoptotic process allowing continued growth of unwanted cells.

It appears that one way of treating hyperproliferative diseases would be by influencing directly the mechanisms by which the cell regulates and effects apoptosis, and even to induce specifically an apoptotic response in hyperproliferative cells. Indeed, the capacity to induce an apoptotic response in tumor cells might determine the efficacy of the treatment.

It is an object of the present invention to provide a method of treating hyperproliferative diseases.

It is another object of the present invention to provide a method of treating hyperproliferative diseases by influencing directly the mechanisms by which the cell regulates and effects apoptosis.

It is still another object of the present invention to provide a method of treating hyperproliferative diseases by inducing specifically an apoptotic response in hyperproliferative cells.

It is a further object of the present invention to provide compounds for use in the above-mentioned methods.

SUMMARY OF THE INVENTION

The present invention is based on the surprising discovery that inhibition (silencing) of the gene Wrap53 (Genbank Accession No. NM_018081) results in massive cell apoptosis.

The Wrap53 protein has been reported to be upregulated in parathyroid (Velazquez-Fernandez et al., World J Surg, Apr. 20, 2006) and brain tumors (Zhang, Bioinformatics, (20) p 2390-8, 2004), which is in line with data for other cytokinesis-specific proteins such as Aurora A/B and Rho/Rac that are often overexpressed in cancer (Fu, Mol Cancer Res, (5) p 1-10, 2007).

Little has been known about the function of the Wrap53 protein. However, the present inventors have found that the Wrap53 protein is induced during the G2 phase of the cell cycle and is recruited to the midbody during cytokinesis. Cytokinesis is the final stage of cell division and the mechanism underlying this process remains one of the major unsolved questions in basic cell biology. Wrap53-depleted cells have been found to arrest in G2/M and ultimately die by apoptosis.

Furthermore, the inventors have found that human tumor cell lines are more sensitive to silencing of the Wrap53 gene, compared to healthy human cells, such as normal human fibroblasts. While not wishing to be bound to any particular theory, it is surmised that this is due to the involvement of Wrap53 in cell division.

Based on this discovery, the present inventors now have developed a new method of inducing cellular apoptosis for use in the treatment of hyperproliferative disorders.

The inventive method is independent of p53 status in the cell, which may be an important advantage in the treatment of cancer.

Thus, the present invention is based on inhibition of the gene Wrap53 as a new method of treatment of hyperproliferative conditions. The treatment according to the present invention is especially effective for the destruction of hyperproliferating cells, at relatively low doses. According to a first aspect the present invention provides a small nucleic acid molecule suitable for reducing the expression of the gene Wrap53, for use as a medicament.

According to a second aspect the present invention provides a small nucleic acid molecule suitable for reducing the expression of the gene Wrap53, for use as a medicament in the treatment of a hyperproliferative conditions.

According to one other aspect the invention relates to the use of a small nucleic acid molecule, in the manufacture of a medicament for treating a hyperproliferative condition.

In one embodiment, the small nucleic acid molecule is a small single-stranded, double-stranded or partly double-stranded nucleic acid molecule that down-regulates expression of Wrap53 gene via RNA interference (RNAi), wherein at least one strand of said small nucleic acid molecule is about 15 to about 30 nucleotides in length; and wherein at least one strand of said small nucleic acid molecule comprises a nucleotide sequence having sufficient complementarity to an RNA of said Wrap53 gene for the small nucleic acid molecule to direct cleavage of said RNA via RNA interference, for use as a medicament.

In one embodiment, the small nucleic acid molecule is a small double-stranded or partly double-stranded nucleic acid molecule that down regulates expression of Wrap53 gene via RNA interference (RNAi), wherein each strand of said small nucleic acid molecule is independently about 15 to about 30 nucleotides in length; and wherein one strand of said small nucleic acid molecule comprises a nucleotide sequence having sufficient complementarity to an RNA of said Wrap53 gene for the small double-stranded nucleic acid molecule to direct cleavage of said RNA via RNA interference.

In one embodiment, the present invention provides a method of inhibiting the hyperproliferative cellular activity associated with neoplasms and with various hyperproliferative diseases, by inducing apoptosis in the hyperproliferative cells.

Further aspects and embodiments of the invention are as defined in the claims.

DETAILED DESCRIPTION OF THE INVENTION

Inhibiting expression of a gene, also termed gene silencing, may be achieved by means of the so called RNA interference (RNAi) technique (cf. e.g. Zamore et al., 2000, Cell, 101, 25-33; Fire et al., 1998, Nature, 391, 806; Sharp, 1999, Genes & Dev., 13:139-141; and Strauss, 1999, Science, 286, 886).

In RNAi a double-stranded RNA (dsRNA) sequence corresponding to a sequence of a gene interferes with and reduces the expression of this gene. In short, on introduction of a dsRNA into a cell the dsRNA is cleaved by a ribonuclease III enzyme, called Dicer, into dsRNA fragments having a length of approximately 19-23 by (base pairs), so-called short interfering RNAs (siRNAs). The siRNA forms a complex with further cellular proteins, called the RNA-induced silencing complex (RISC). Via an ATP-dependent mechanism, siRNA within RISC is unwound and then hybridizes with a complementary RNA, which may be a mature mRNA resulting from transcription of the target gene to be silenced. The hybrid dsRNA then is cleaved by an endoribonuclease. However, the activated RISC not only may result in degradation of specific mRNA, but also may block translation of the specific mRNA by binding to ribosomes as well as being capable of migrating into the nucleus and bind to the complementary DNA, thereby leading to reduced transcription of the target gene.

It has been shown that in both animals and plants, two distinct pathways exist, wherein RNAs of 21 to 23 nucleotides in length function as post-transcriptional regulators of gene expression. Small interfering RNAs (siRNAs) act as mediators of sequence-specific mRNA degradation in RNA interference (RNAi) whereas miRNAs regulate developmental timing by mediating sequence-specific repression of mRNA translation. As indicated herein above, siRNAs are believed to be double-stranded, while miRNAs are single-stranded (cf e.g. A. E. Pasquinelli et al., Nature 408, 86 (2000)).

Since its discovery some years ago much work has been devoted to RNAi, and it is considered to be a valuable tool in the genetic research area as well as a promising tool for gene therapy. In particular, very advantageously, the siRNA has been show to be highly specific in its interaction with the gene to which it corresponds. Also, it has been found that an amplification mechanism allows efficient interference to be obtained from only a few dsRNA molecules.

For the purpose of the present invention, and unless the contrary is not clearly obvious form the context, any reference to the Wrap53 gene should be construed to include the gene sequence under Genbank Accession No. NM_018081 as well as any allele thereof.

By "inhibit", "down-regulate", "silence" or "knock-down" etc. it is meant that the expression of the gene, or level of the corresponding RNAs, is reduced below that observed in the absence of the nucleic acid molecules of the invention.

The small nucleic acid molecule of the invention should be construed as any nucleic acid molecule or nucleic acid-containing molecule, e.g. a chemically modified derivative thereof, capable of inhibiting or down-regulating the expression of a Wrap53 gene within a mammalian cell or a living organism, e.g. a human.

Thus, the small nucleic acid molecules of the invention may be e.g. a short interfering nucleic acid (siNA), short interfering RNA (siRNA), double-stranded RNA (dsRNA), micro-RNA (miRNA), and short hairpin RNA (shRNA), capable of inhibiting or down-regulating the expression of Wrap53 gene expression.

For example the small nucleic acid molecule can be a double-stranded polynucleotide molecule comprising self-complementary sense and antisense regions, wherein the antisense region comprises nucleotide sequence that is complementary to a nucleotide sequence in a Wrap53 gene.

The small nucleic acid molecule can comprise two separate, complementary oligonucleotides. Alternatively, the small nucleic acid molecule comprises a single oligonucleotide, having complementary regions linked by means of a nucleic acid based or non-nucleic acid-based linking moiety or moieties, as taught in e.g. US 2006/0025361 or US 2006/0063174.

Thus, the small nucleic acid molecule of the invention may be a polynucleotide with a duplex, asymmetric duplex, hairpin or asymmetric hairpin secondary structure, or a circular single-stranded polynucleotide having two or more loop structures and a stem comprising self-complementary sense and antisense regions.

The small nucleic acid molecule of the invention may have a length of e.g. 15 nucleotides to 30 nucleotides or more, e.g. comprising at least 16, 17, 18, 19, 20, 21 or 22 nucleotides and less than 30, 29, 28, 27, 26, 25, 24, or 23 nucleotides.

In one embodiment, the small nucleic acid molecule of the invention is a precursor molecule, having a length of up to e.g. 50-100 nucleotides.

In one embodiment of a double stranded nucleic acid molecule the invention, at least one strand, more preferably both strands, have a 3' overhang of from about 1 to about 6 nucleotides in length, e.g. 1-5, 1-4 or 2-3 nucleotides in length. If both strands have an overhang, then the length of these overhangs may be the same or different.

The nucleotides according to the invention comprises the natural nucleotides A, C, G and U as well as other nucleotide analogs, e.g. synthetic non-naturally occurring nucleotide analogs. Further nucleobases may be substituted by corresponding nucleobases capable of forming analogous H-bonds to a complementary nucleic acid sequence, e.g. U may be substituted by T.

In one embodiment, the small nucleic acid molecule is chemically modified. Chemical modifications that may be applied to the small nucleic acid molecule of the invention as well as methods for performing said modifications are described e.g. in US patent application of publication number 2006/0025361, the entire contents of which is incorporated herein by reference. For example, in said US application, chemical modifications such as phosphorothioate internucleotide linkages, 2'-deoxyribonucleotides, 2'-O-methyl ribonucleotides, 2'-deoxy-2'-fluoro ribonucleotides, 4'-thio ribonucleotides, 2'-O-trifluoromethyl nucleotides, 2'-O-ethyl-trifluoromethoxy nucleotides, 2'-O-difluoromethoxy-ethoxy nucleotides etc are disclosed, and it is mentioned that such chemical modifications, when used in various siRNA constructs, are shown to preserve RNAi activity in cells while at the same time dramatically increasing the serum stability of these compounds. Also, according to said US application other in vitro or in vivo characteristics may be improved by means of such chemical modification, e.g. stability, activity, toxicity, immune response, and/or bioavailability.

It will be readily apparent to the person skilled in the art that the small nucleic molecule according to the invention must have sufficient homology to the targeted Wrap53 mRNA. By "sufficient homology" is meant that the homology should be such as to permit the small nucleic acid molecule to hybridize specifically to Wrap53 mRNA. In other words, at least one strand of a small nucleic acid molecule of the invention should comprise a nucleotide sequence having sufficient complementarity to RNA of said Wrap53 gene for the small double-stranded nucleic acid molecule to direct cleavage of said RNA via RNA interference.

"Complementarity" refers to the ability of a nucleotide sequence to form hydrogen bond(s) with another nucleotide sequence by either traditional Watson-Crick or other non-traditional types. A percent complementarity indicates the percentage of contiguous residues in a nucleotide sequence which can form hydrogen bonds (e.g., Watson-Crick base pairing) with a second nucleotide sequence. For example, in a sequence of 10 nucleotides, a 70% complementarity with a second nucleotide sequence would correspond to 7 contiguous residues of the 10-nucleotide sequence forming hydrogen bonds with 7 contiguous residues of the second nucleotide sequence.

"Perfect complementarity" means that all the contiguous residues of a nucleic acid sequence will hydrogen bond with the same number of contiguous residues in a second nucleic acid sequence, i.e. 100% complementarity.

In one embodiment of the invention, the small nucleic acid comprises a nucleotide sequence of at least 10, 11, 12, 13, 14, 15, 16, 17, 18, 19, 20, 21, 22, 23, 24, 25, 26, 27, 28, 29 or 30 nucleotides having a complementarity with a target sequence of Wrap53 mRNA of at least 50%, or at least 60%, at least 70%, at least 80%, at least 90%, or at least 95%.

In one embodiment of the invention, the small nucleic acid molecule comprises a nucleotide sequence of at least 10, 11, 12, 13, 14, 15, 16, 17, 18, 19, 20, 21, 22, 23, 24, 25, 26, 27, 28, 29 or 30 nucleotides having a perfect complementarity with a target sequence of Wrap53 mRNA.

The small nucleic acid of the invention may be prepared, for example, via chemical synthesis, in vitro transcription, enzymatic digestion of a longer dsRNA using an RNase III enzyme such as Dicer or RNase III, expression in cells from an siRNA expression plasmid or viral vector, or expression in cells from a PCR-derived siRNA expression cassette, or by a combination of any of these methods.

The above-mentioned methods are generally well-known to the person skilled in the art and relevant descriptions may be found, for example, at http://www.bdbiosciences.com, http://www.oligoengine.com, http://www.ambion.com/techlib/tn/103/2.html, http://www.genetherapysystems.com, www.dharmacon.com, http://www.mpibpc.gwdg.dc/abteilungen/100/105/sirna.html, and/or in the references cited therein, which references are also incorporated herein by reference.

In one embodiment of the invention, the small nucleic acid molecule of the invention is chemically prepared. In this embodiment, the 2' hydroxyls may be protected against degradation during synthesis, using, for example, acid labile orthoester protecting groups (see Scaringe et al, J. Am. Chem. Soc. 120:11820 (1998) and www.dharmacon.com (e.g., the ACE technology described therein)).

In another embodiment of the invention the small nucleic acid molecule is prepared by enzymatic digestion, starting from a longer dsRNA and using an RNase III type enzyme, such as Dicer. For example, Gene Therapy Systems Inc. provides a Dicer siRNA generation kit that may be used according to the invention.

The small nucleic acid molecule of the invention can also be prepared by a recombinant method. By such method in vivo transcription in e.g. mammalian cells is obtainable. The skilled person will be well aware of suitable vectors, e.g. vectors containing RNA polymerase III or U6 promoter sequences, that may be used as expression vectors or as shuttle vectors in conjunction with suitable viral systems to introduce small nucleic acid molecule of the invention into mammalian cells. The vectors also may be engineered to express sense and anti-sense strands of siRNAs that anneal in vivo to produce functional siRNAs.

Short hairpin RNA can be prepared e.g. by inserting into a vector a target sequence of e.g. 19-23 nucleotides of the sense strand of the Wrap53 gene, followed by a short spacer sequence of e.g. 3-9 nucleotides, followed by a sequence of e.g. 19-23 nucleotides of the antisense strand of the Wrap53 gene and a transcription terminator, e.g. a poly-U sequence of e.g. 5-7 nucleotides.

In general, nucleic acid molecules can be administered to cells by a variety of methods known to the person skilled in the art. Examples of such methods include encapsulation in liposomes or other vehicles such as such as hydrogels, cyclodextrins, biodegradable nanocapsules and bioadhesive microspheres. The combination of nucleic acid and vehicle may be locally delivered by direct injection or by use of an infusion pump. Further descriptions of nucleic acid delivery and administration are provided in the PCT applications WO 94/02595, WO93/23569, WO99/05094, and WO99/04819, the teachings of which are incorporated by reference herein.

Furthermore, US patent application of publication number 2006/0063174 addresses the problem of providing compositions and methods to efficiently express and deliver siRNA intracellularly in mammalian cells, such compositions being of use e.g. in therapy for genetic diseases. In said patent application, the contents of which is incorporated herein by reference, expression cassettes comprising a gene encoding a siRNA, vectors comprising such expression cassettes as well as methods for their preparation are described. Said expression systems are contemplated as potentially useful also for the purpose of the present invention, and having regard to the teachings of the US patent application as well as of the prior art documents referred to therein the skilled person will be able to design a suitable system for delivery to a mammal of a small nucleic acid molecule according to the invention.

US patent application of publication number 2006/0035815 discloses pharmaceutical compositions for administration of a double stranded ribonucleic acid (dsRNA) molecule to an animal, comprising the dsRNA molecule and a peptide of about 5 to about 40 amino acids consisting of all or part of a certain amino acid sequence. The polynucleotide delivery-enhancing polypeptide as disclosed in said patent application is contemplated as useful for delivery of a small nucleic acid according to the present invention to a mammal, and the entire contents of said US patent application are incorporated herein by reference.

In one embodiment of the invention, a pharmaceutical composition is provided, comprising a pharmaceutically effective dose of the small nucleic acid according to the invention and a pharmaceutically acceptable excipient.

A pharmaceutical composition, as used herein, refers to a composition in a form suitable for administration, e.g., systemic administration, to a mammal subject, preferably a human.

In one embodiment, the pharmaceutical composition of the invention includes a pharmaceutically effective amount of the nucleic acid molecules of the invention in a pharmaceutically acceptable carrier or diluent, suitable for storage or administration. Pharmaceutically acceptable excipients, such as carriers or diluents for therapeutic use are well known in the pharmaceutical art, and are described, for example, in the latest edition of Remington's Pharmaceutical Sciences, Mack Publishing Co. hereby incorporated by reference.

A pharmaceutically effective dose, as used according to the present invention, is that dose required to provide a beneficial effect to a treated subject, e.g. to prevent, alleviate or cure a hyperproliferative condition. The pharmaceutically effective dose depends on the type of hyperproliferative condition, the composition used, the route of administration, the physical characteristics of the treated subject, concurrent medication etc.

As a general indication, amounts of siRNA of 250 μg/kg of body to 2 mg/kg have been administered to mice with a good effect and without any toxic effect (Song et al. Nat. Med, 2003, 9:347-351). In monkey, a dosage of siRNA of 10-40 mg/kg of body weight been tested without any toxicity (Li et al. Nat. Med, 2005, 11:944-951). Quinlan, E. (2005) ARVO Annual Meeting, 1-5 May, Ft Lauderdale, Fla., USA reports treating 14 human subjects with single, intravitreal doses of 100-800

It is contemplated that the nucleic acid molecules of the invention will be administered by any suitable method, e.g. orally, topically, parenterally, by inhalation or spray or rectally in dosage unit formulations containing conventional non-toxic pharmaceutically acceptable carriers, adjuvants and vehicles. Parenteral administration may be effected e.g. by percutaneous, subcutaneous, intravascular (e.g., intravenous), intramuscular, or intrathecal injection or infusion techniques.

Hyperproliferative conditions that may be treated according to the invention comprise any type of hyperproliferative condition, e.g. a malignant hyperproliferative disorder such as a cancer, neoplasia tumor or carcinoma.

It is contemplated that any type of cancer may treated by a method of the invention, e.g. breast cancer, brain tumors, melanoma, leukemia, bladder cancer, prostatic cancer, cervical cancer, osteosarcoma, colon cancer, colorectal cancer, gastric cancer, endometrial cancer, glioma, lymphoma, eye cancer, liver cancer, oral cancer, ovarian cancer, testicular cancer etc.

In one embodiment of the invention the treatment of the mammal is a combination treatment, wherein treatment with the small nucleic acid molecule of the invention is combined with treatment with at least one other therapeutically active agent. It is contemplated that each component may be administered at the same time or sequentially in any order at different points in time. Thus, each component can be administered separately but sufficiently closely in time so as to provide the desired therapeutic effect.

Figure 4:
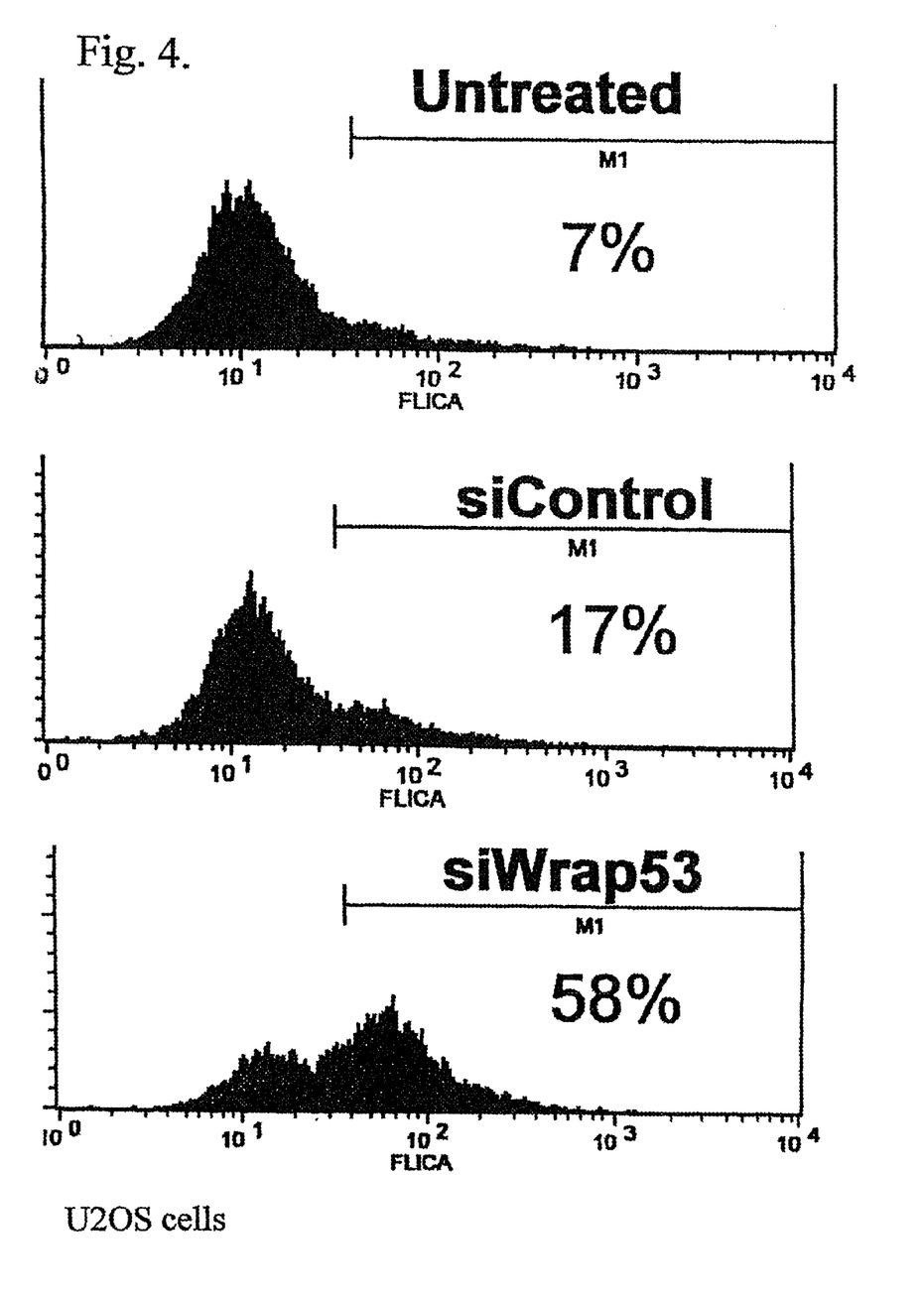
FIG. 4. Apoptosis analysis of human osteosarcoma cells (U2OS) treated with siWrap53 oligonucleotides. Apoptosis is shown in % and was measured by FLICA staining (pan-caspase) followed by FACS analysis.
Figure 5:
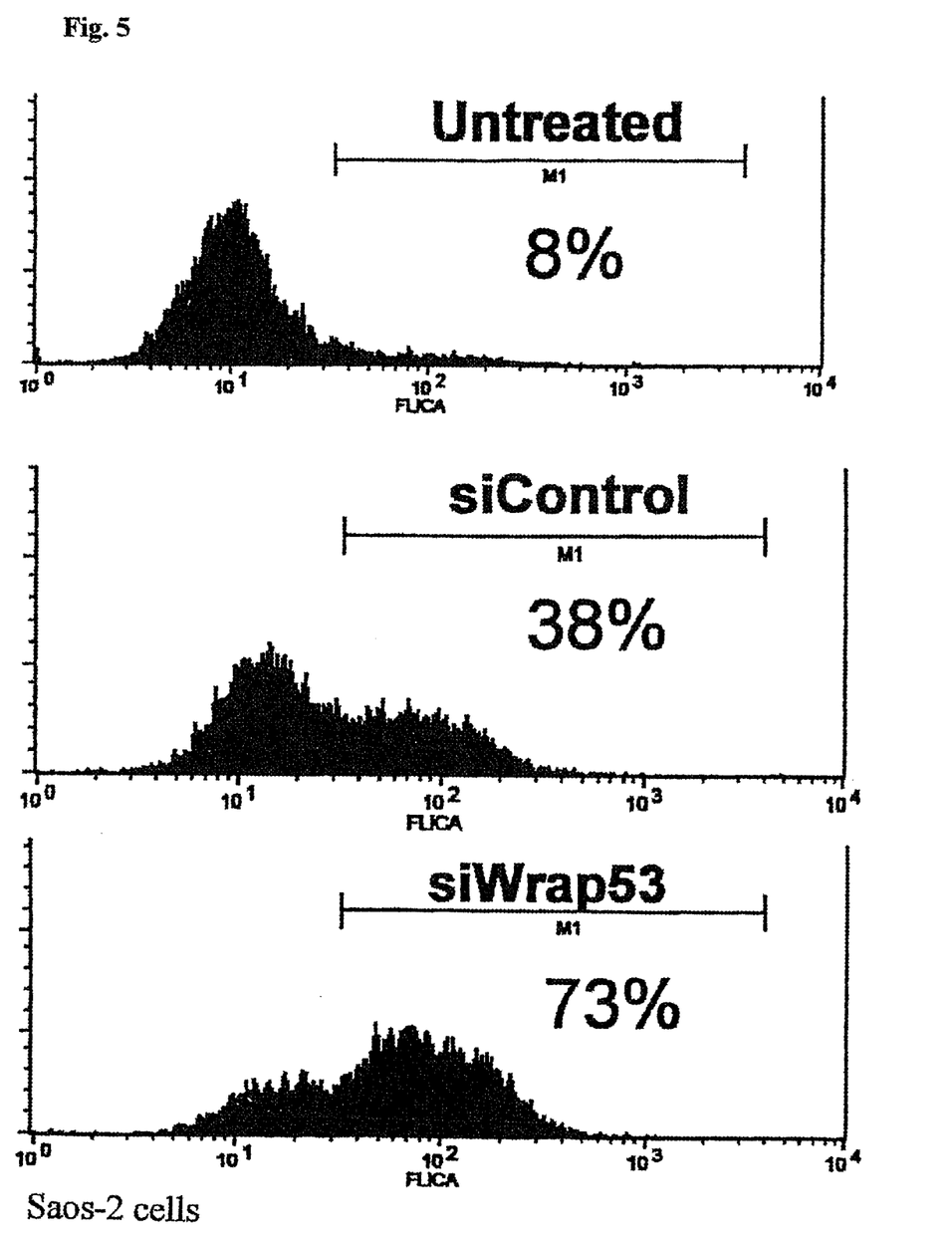
FIG. 5. Apoptosis analysis of another human osteosarcoma cell line (Saos-2) treated with siWrap53 oligonucleotides. Apoptosis is shown in % and was measured as described in Example 4.
Figure 9:
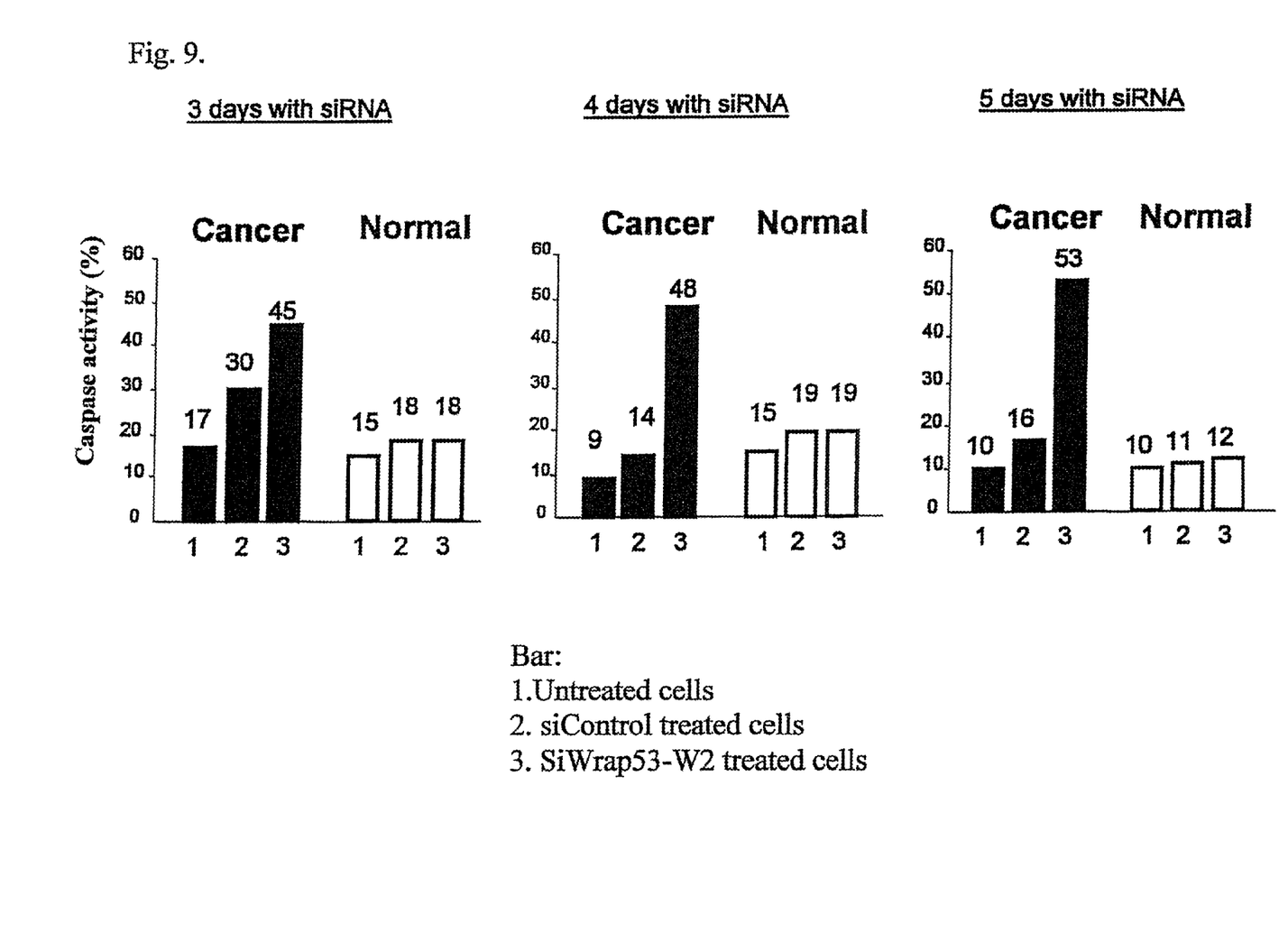
FIG. 9. Apoptosis analysis of U2OS (cancer cells) and IMR-90 (normal fibroblasts) cells treated with siWrap53 oligonucleotides. Apoptosis is shown in % and was measured as described in Example FIG. 4.

In one preferable embodiment, the other therapeutically active agent in a combination treatment is an anticancer agent, such as Gleevec® (imatinib mesylate), Sutent® (sunitinib malate), Avastin® (bevacizumab), paclitaxel, doxorubicin and cisplatin. Apoptosis mediated by inhibition of Wrap53 may be assessed by measuring the amount of active caspases, which are active only in apoptotic cells. Several human tumor cell lines have been analysed for sensitivity to siRNA-mediated down-regulation of Wrap53 using the above mentioned method. These cell lines include U2OS (human osteosarcoma), Saos-2 (human osteosarcoma), MCF-7 (human breast cancer), HCT116 (human colon cancer), H1299 (human lung cancer) and IMR-90 (human lung fibroblasts) and the results thereof are illustrated in FIGS. 4-5 and 9.

The exact mechanism of Wrap53-mediated apoptosis protection is not known. However, the present inventors found that knock-down of Wrap53 resulted in apoptosis in all cancer cell lines tested in a dose dependent manner. Interestingly, this effect is p53-independent since p53 null cells also die to the same extent. p53 is an important player in the onset of apoptosis and many cancer drugs act through activation of the p53 pathway, subsequently inducing cell death.

One drawback with these conventional drugs is that p53 is non-functional in around 50% of all human tumors, which reduces the efficiency of the treatment considerably. The fact that apoptosis induced by down-regulation of Wrap53 is independent of p53 can therefore be considered an important advantage.

EXAMPLES

The following are non-limiting examples showing the selection, isolation, synthesis and activity of the small nucleic acids of the invention.

Example 1

Identification of Potential Target Sites in Human Wrap53 RNA

The sequence of human Wrap53 gene is screened for accessible sites using a computer-folding algorithm: Ambion siRNA target finder (http://www.ambion.com/techlib/misc/siRNA_finder.html).

The sequences of a number of binding sites are shown in Table I.

TABLE 1

| Wrap53 siRNA | Target sequence (21 bp) 5'→23' | |
|---|---|---|
| siWrap53-57 | AAAACTTTTAGCGCCAGTCTT | (SEQ ID NO: 1) |
| siWrap53-94 | AAAACCCCAATCCCATCAACC | (SEQ ID NO: 2) |
| siWrap53-1B | AACACAGTGCTTTCAAAAGAA | (SEQ ID NO: 3) |
| siWrap53-500 | AACCTGAGAACTTCTTGAAAG | (SEQ ID NO: 4) |
| siWrap53-665 | AAGGTGATACCATCTATGATT | (SEQ ID NO: 5) |
| siWrap53-E9 | AATCAGCGCATCTACTTCGAT | (SEQ ID NO: 6) |
| siWrap53-E13 | AATGTCGGCTTCAGCTCTGGT | (SEQ ID NO: 7) |
| siWrap53-W2 | AACGGGAGCCTTTCTGAAGAA | (SEQ ID NO: 8) |

Example 2

Synthesis and Purification of siRNA Oligonucleotides Targeting Wrap53 RNA siRNA oligonucleotides are designed to anneal to various sites in the mRNA. The siRNA oligonucleotides were synthesized and purified using the Silencer® siRNA Construction Kit (Ambion).

The sequences of a number of chemically synthesized antisense constructs used in this study are complementary sequences to the target sequences shown in Table I.

Example 3

Selection of siRNA Oligonucleotides Efficient in Knocking Down Wrap53 Expression (Also Called siWrap53 Oligonucleotides)

siRNA nucleic acid molecules targeted to the human Wrap53 mRNA are designed and synthesized as described above. These siRNAs can be tested for activity in vitro, for example, using the following procedures: siRNA oligonucleotides are transfected into cells using the transfections agent Oligofectamine (Invitrogen) and cells are grown for 48-72 hours post-transfection. Cells are harvested, and RNA and protein are purified using Trizol (Invitrogen) and further evaluated by Northern and Western blot analyses. To detect Wrap53 RNA, a Wrap53-specific probe is radioactively labelled and hybridized to the Northern blot filter. Wrap53 protein is detected using an anti-Wrap53 antibody. The efficiency of siWrap53 oligonucleotides are determined by Wrap53 RNA and Wrap53 protein levels after 48-72 hours of siWrap53 treatment as compared with either untransfected cells or cells transfected with siControl oligonucleotide (which is a scrambled 21-nt sequence not homologous to any gene).

Figure 1:
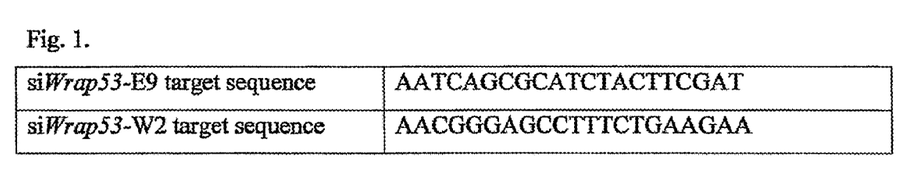
FIG. 1. The target sequences, siWrap53-E9 (SEQ ID NO:6) and siWrap 3-W2 (SEC) ID NO:8), of the optimal siRNA oligonucleotides for knock-down of Wrap53.
Figure 2:
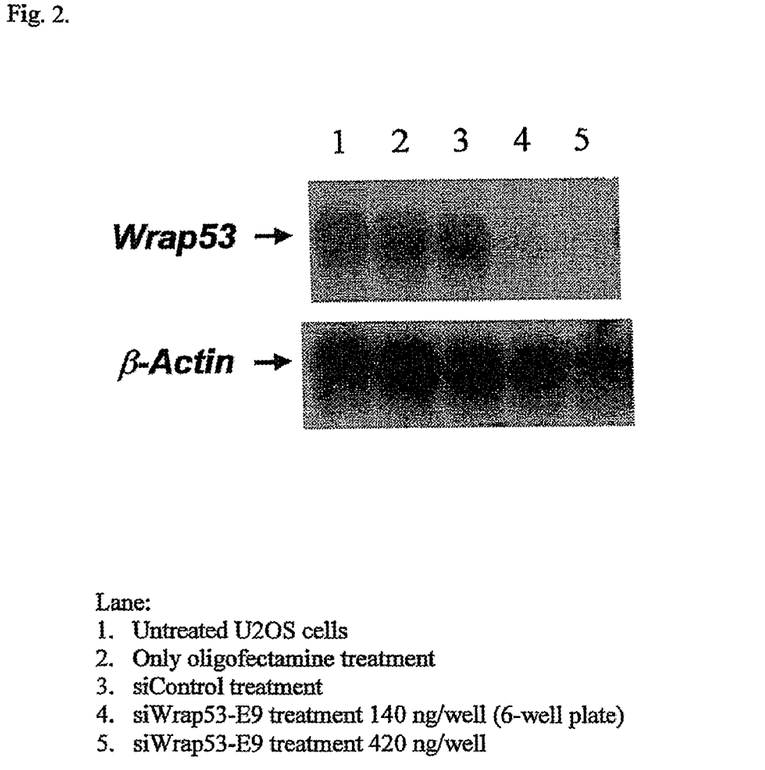
FIG. 2. Northern blot showing Wrap53 RNA levels after treatment with siWrap53 siRNA oligonucleotides.

Northern blot results are represented in FIG. 2, wherein the lanes show (in lane number order): 1. Untreated U2OS cells. 2. U2OS cells treated only by oligofectamine. 3. U2OS cells treated by an siControl sequence. 4. U2OS cells treated by siWrap53-E9, 140 ng/well. 5. U2OS cells treated by siWrap53-E9 420 ng/well.

Figure 3:
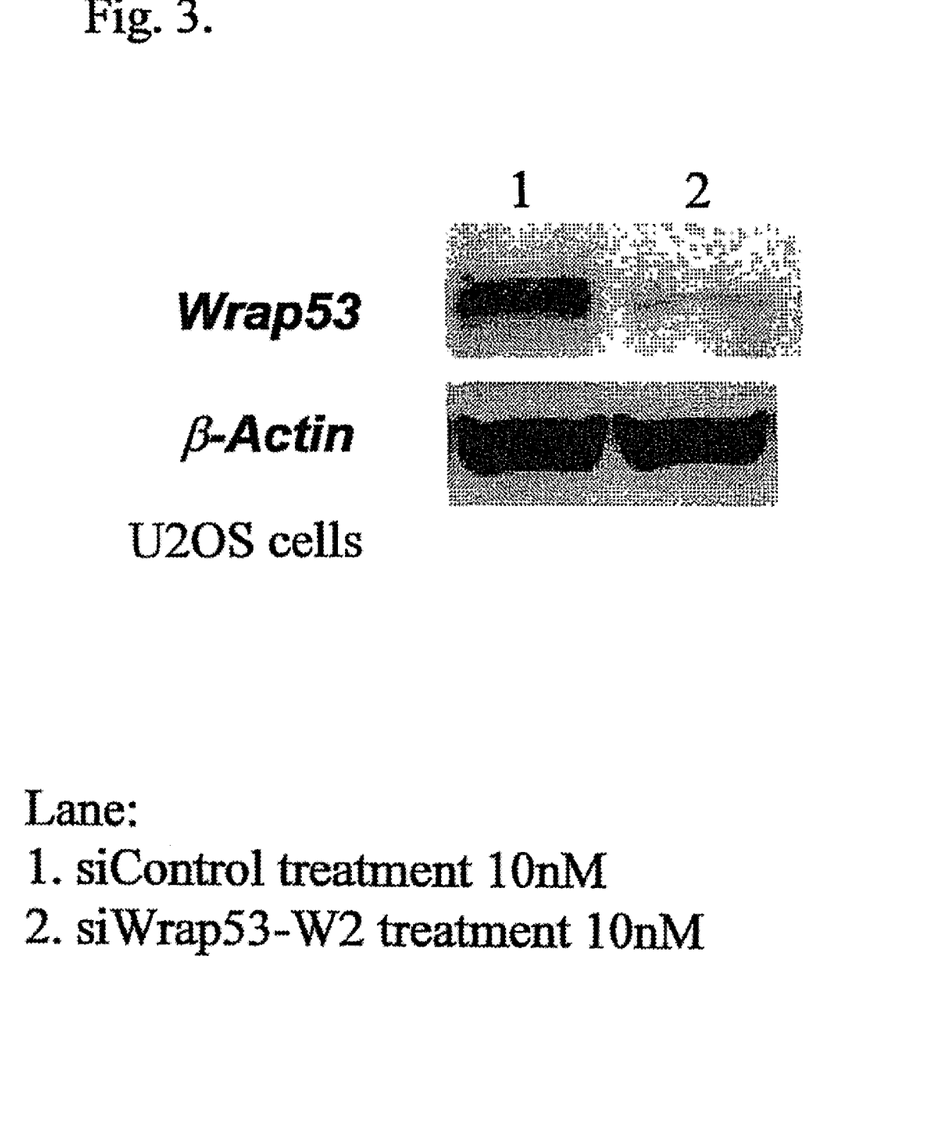
FIG. 3. Western blot showing Wrap53 protein levels after treatment with siWrap53 oligonucleotides.

FIG. 3 represents Western blot, wherein the lanes show (in lane number order): 1. Results obtained from treatment of U2OS cells with siControl, 10 nM. 2. Results obtained from treatment of U2OS cells with siWrap53-W2, 10 nM.

It may be noted that the amino acid sequence of the Wrap53 protein is known and can be found in the UniProt database (http://www.ebi.uniprot.org/index.shtml), under accession number Q9BUR4.

Example 4

Apoptosis Assay to Evaluate Cell Death after the Down-Regulation of Wrap53 Gene Expression To assess apoptosis, siWrap53 treated cells were harvested by trypsinization and labeled with FAM-VAD-FLICA (Fluorochrome Inhibitors of Caspases) which detects active caspases, according to the manufacturer's recommendations (Chemicon). Samples were analysed on a FACS Calibur flow cytometer (Becton Dickinson) using the CellQuest™ software.

In FIGS. 4, 5 and 9 apoptosis results obtained using different human osteosarcoma cells are shown.

Example 5

Figure 6:
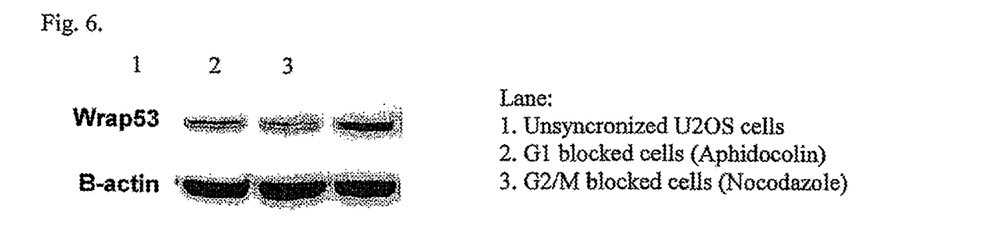
FIG. 6. Western blot showing Wrap53 protein levels at different cell cycle phases. Wrap53 levels are higher in cells arrested in G2/M phase.

Cell Cycle Blockage of Cells to Evaluate Induction of Wrap53 Protein at Different Cell Cycle Phases To block cells at G1 and G2/M phase cells were treated with the drugs Aphidocolin and Nocadozole, respectively, for 24 hours. Cells were harvested and proteins were isolated and further analysed by Western blot analysis using a Wrap53-specific antibody. FIG. 6 represents Western blots, showing Wrap53 protein levels at different cell cycle phases. It can be seen that Wrap53 levels are higher in cells arrested in G2/M phase.

Example 6

Cell Cycle Analysis to Evaluate Cell Cycle Effects Upon Wrap53 Knock-Down

Figure 8:
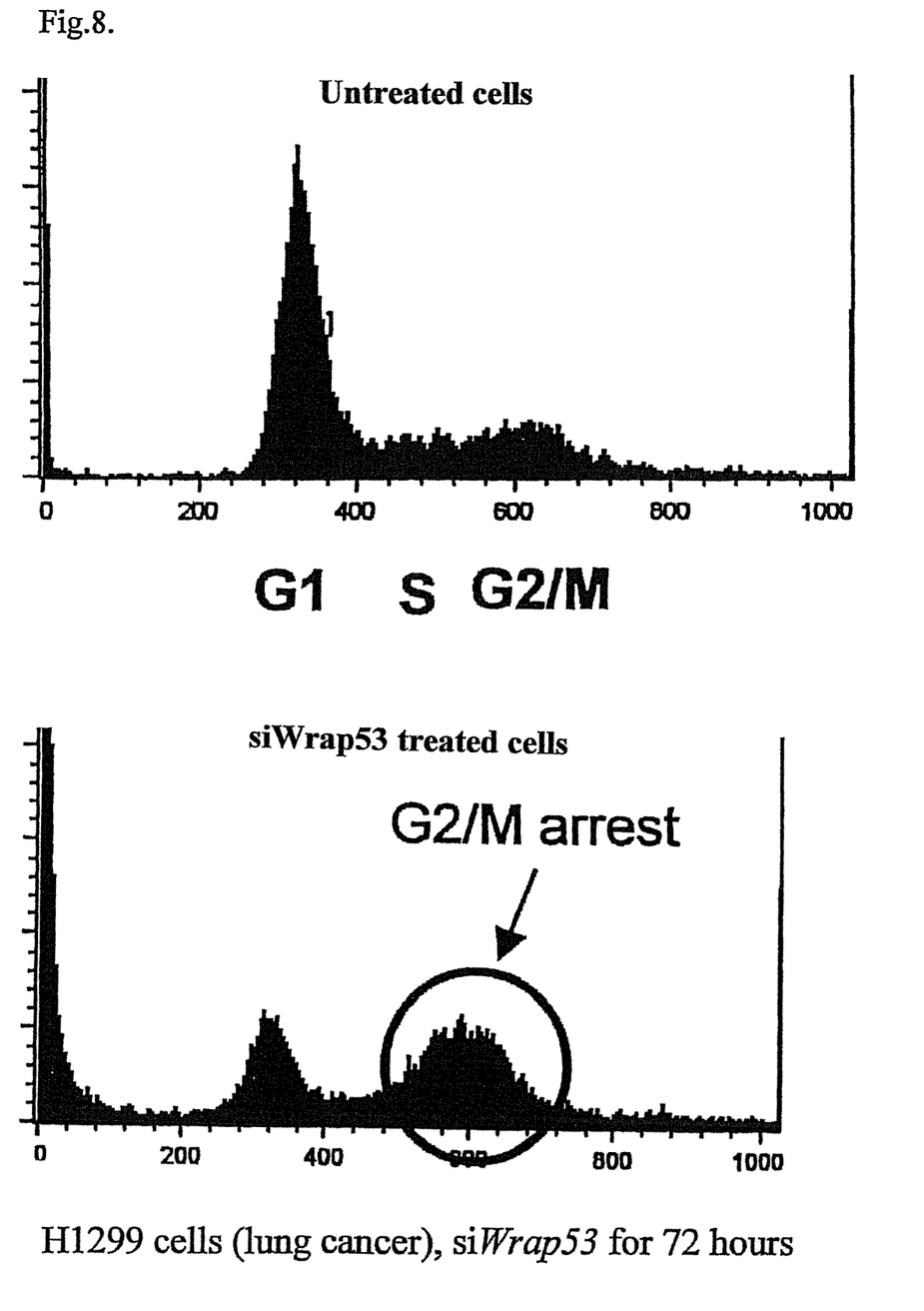
FIG. 8. Cell cycle analysis of H1299 cells by Propidium Iodide (PI) staining followed by FACS analysis after siWrap53 treatment.

Cell cycle effects were assessed by Propidium iodide (PI) staining followed by FACS analysis. PI intercalates into double-stranded nucleic acids, such as DNA, and the amount of DNA per cells further reveals what cell cycle phase the cell is in. Results obtained by siWrap53 treatment of human lung cancer cells are shown in FIG. 8. From the results, it is clear that the cells treated by siWrap53 are arrested in the G2/M phase.

Example 7

Immunostaining to Analyse the Cellular Localization of the Wrap53 Protein

Figure 7:
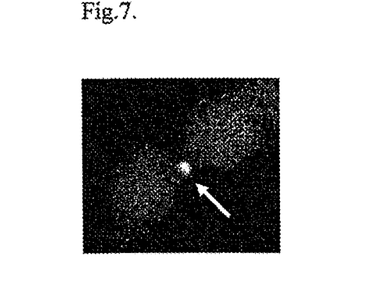
FIG. 7. Immunostaining of Wrap53 protein in a dividing cell. The location of Wrap53 is shown as a white dot between the cells, as indicated by the arrow.

To detect the location of Wrap53 in cells, a Wrap53 specific antibody is added to fixed cells grown on slides according to standard procedures. After binding to intracellular Wrap53 proteins, the Wrap53 antibody is visualized using a fluorescently labeled secondary antibody that binds to the Wrap53 antibody. FIG. 7 shows the results obtained by thus immunostaining Wrap53 protein in a dividing cell. The location of Wrap53 protein is seen as a white dot between the cells (as indicated by the arrow).

The invention claimed is:

1. An isolated small nucleic acid molecule that down-regulates protein expression of the Wrap53 gene via RNA interference (RNAi), wherein at least one strand of said small nucleic acid molecule is about 15 to about 30 nucleotides in length; and wherein at least one strand of said small nucleic acid molecule comprises a nucleotide sequence having sufficient complementarity to an RNA of said Wrap53 gene for the small nucleic acid molecule to direct cleavage of said RNA via RNA interference.

2. The small nucleic acid molecule of claim 1, selected from a short interfering nucleic acid (siNA), a short interfering RNA (siRNA), a double-stranded RNA (dsRNA), a micro-RNA (miRNA), and a short hairpin RNA (shRNA).

3. The small nucleic acid of claim 1, which is double-stranded.

4. The small nucleic acid of claim 1, comprising a nucleotide sequence of 10-30 nucleotides having a complementarity with a target sequence of Wrap53 mRNA of at least 50%.

5. The small nucleic acid molecule of claim 4, comprising a nucleotide sequence of 10-30 nucleotides having a complementarity with a target sequence of Wrap53 mRNA of at least 90%.

6. The small nucleic acid molecule of claim 4, comprising a nucleotide sequence of 10-30 nucleotides having a 100% complementarity with a target sequence of Wrap53 mRNA.

7. The small nucleic acid of claim 4, wherein the target sequence comprises a sequence selected from any one of the following SEQ ID NOS:

```
SEQ ID NO 3:
(siWrap53-1B)      AACACAGTGCTTTCAAAAGAA;

SEQ ID NO 4:
(siWrap53-500)     AACCTGAGAACTTCTTGAAAG;

SEQ ID NO 5:
(siWrap53-665)     AAGGTGATACCATCTATGATT;

SEQ ID NO 6:
(siWrap53-E9)      AATCAGCGCATCTACTTCGAT;

SEQ ID NO 7:
(siWrap53-E13)     AATGTCGGCTTCAGCTCTGGT; and

SEQ ID NO 8:
(siWrap53-W2)      AACGGGAGCCTTTCTGAAGAA.
```

8. A pharmaceutical composition comprising a small nucleic acid molecule according to claim 1 and a pharmaceutically acceptable excipient.

9. A method for treatment of a hyperproliferative condition, comprising administering to a mammal in need of such treatment a therapeutically effective amount of the small nucleic acid molecule of claim 1 to treat the hyperproliferative condition.

10. A method according to claim 9, wherein the hyperproliferative condition is a tumor or cancer.

11. A method according to claim 10, wherein the treatment is a combination treatment with at least one anticancer agent.

12. The method according to claim 11, wherein the at least one anticancer agent comprises a chemotherapeutic drug.

13. The method according to claim 9, wherein the hyperproliferative condition is associated with a lack of functional p53 gene.

14. A method for treatment of a hyperproliferative condition, comprising administering to a mammal in need of such treatment a therapeutically effective amount of small nucleic acid molecule of claim 7 to treat the hyperproliferative condition.

15. A method according to claim 14, wherein the hyperproliferative condition is a tumor or cancer.

16. A method according to claim 15, wherein the treatment is a combination treatment with at least one anticancer agent.

17. The method according to claim 16, wherein the at least one anticancer agent comprises a chemotherapeutic drug.

18. The method according to claim 14, wherein the hyperproliferative condition is associated with a lack of functional p53 gene.

19. The method according to claim 9 wherein the nucleic acid molecule is double-stranded.

20. The method according to claim 14 wherein the nucleic acid molecule is double-stranded.

* * * * *

SEQUENCE LISTING

<160> NUMBER OF SEQ ID NOS: 8

<210> SEQ ID NO 1
<211> LENGTH: 21
<212> TYPE: DNA
<213> ORGANISM: Homo sapiens

<400> SEQUENCE: 1 aaaacttta gcgccagtct t    21

<210> SEQ ID NO 2
<211> LENGTH: 21

```
<212> TYPE: DNA
<213> ORGANISM: Homo sapiens

<400> SEQUENCE: 2
aaaaccccaa tcccatcaac c                                              21

<210> SEQ ID NO 3
<211> LENGTH: 21
<212> TYPE: DNA
<213> ORGANISM: Homo sapiens

<400> SEQUENCE: 3
aacacagtgc tttcaaaaga a                                              21

<210> SEQ ID NO 4
<211> LENGTH: 21
<212> TYPE: DNA
<213> ORGANISM: Homo sapiens

<400> SEQUENCE: 4
aacctgagaa cttcttgaaa g                                              21

<210> SEQ ID NO 5
<211> LENGTH: 21
<212> TYPE: DNA
<213> ORGANISM: Homo sapiens

<400> SEQUENCE: 5
aaggtgatac catctatgat t                                              21

<210> SEQ ID NO 6
<211> LENGTH: 21
<212> TYPE: DNA
<213> ORGANISM: Homo sapiens

<400> SEQUENCE: 6
aatcagcgca tctacttcga t                                              21

<210> SEQ ID NO 7
<211> LENGTH: 21
<212> TYPE: DNA
<213> ORGANISM: Homo sapiens

<400> SEQUENCE: 7
aatgtcggct tcagctctgg t                                              21

<210> SEQ ID NO 8
<211> LENGTH: 21
<212> TYPE: DNA
<213> ORGANISM: Homo sapiens

<400> SEQUENCE: 8
aacgggagcc tttctgaaga a                                              21
```